United States Patent [19]

Eckels

[11] 4,194,502
[45] Mar. 25, 1980

[54] EXTERNALLY APPLIED SUPPORT FOR A PENIS

[76] Inventor: John F. Eckels, 981 Deltona Blvd., Deltona, Fla. 32725

[21] Appl. No.: 24,310

[22] Filed: Mar. 27, 1979

[51] Int. Cl.² ............................................. A61F 5/00
[52] U.S. Cl. ....................................................... 128/79
[58] Field of Search ......................................... 128/79

[56] References Cited

U.S. PATENT DOCUMENTS

| | | | |
|---|---|---|---|
| 1,346,463 | 7/1920 | Renois | 128/79 |
| 1,362,398 | 12/1920 | Crawford et al. | 128/79 |
| 3,131,691 | 5/1964 | Scott | 128/79 |
| 3,397,689 | 8/1968 | Marcantonio | 128/79 |
| 3,495,588 | 2/1970 | Walters | 128/79 |
| 4,022,196 | 5/1977 | Clinton | 128/79 |

FOREIGN PATENT DOCUMENTS

| | | | |
|---|---|---|---|
| 596763 | 6/1922 | Fed. Rep. of Germany | 128/79 |
| 368352 | 3/1923 | Fed. Rep. of Germany | 128/79 |
| 589978 | 2/1978 | U.S.S.R. | 128/79 |

Primary Examiner—Lawrence W. Trapp
Attorney, Agent, or Firm—Duckworth, Hobby, Allen & Pettis

[57] ABSTRACT

A penis support includes a curved base formed from a section of a resilient tubular member having a first radius equal to the radius of the penis. A resilient first side member joins one side of the base and is formed from a second section of the tubular member. The first side member includes first and second laterally symmetrical brace elements which helically sweep above and away from the base. The first side member is adapted to partially support and encircle a first side of the penis. A resilient second side member joins the second side of the base. This second side member is formed from a third section of the tubular member and includes first and second laterally symmetrical brace elements which helically sweep above and away from the base. The second side member is adapted to partially encircle and support a second side of the penis.

15 Claims, 6 Drawing Figures

EXTERNALLY APPLIED SUPPORT FOR A PENIS

BACKGROUND OF THE INVENTION

1. Field of the Invention

The present invention relates to devices for facilitating sexual intercourse, and more particularly, to an externally supplied support for a penis.

2. Description of the Prior Art

The prior art discloses a variety of devices for either internally or externally increasing the rigidity of a penis.

U.S. Pat. No. 1,362,398 (Crawford) discloses a surgical splint for a penis which includes encircling bands positioned at the front and rear of a rigid member which is positioned adjacent to the ventral side of an individual's penis. This device is longitudinally slipped over a penis and includes an aperture in the front portion thereof.

U.S. Pat. No. 3,495,588 (Walters) discloses a surgical splint having a generally tubular configuration with fully closed side walls. U.S. Pat. No. 3,939,827 (Brunsteter) discloses an erection aid for a penis which includes a splint and a cover which is wrapped around the splint. This device fully encloses a predetermined length of a penis to provide additional support.

U.S. Pat. No. 3,401,687 (Hood) discloses a tubular, expandable member which surrounds and thereby supports a penis.

U.S. Pat. No. 2,868,192 (Dannen) discloses a prosthetic genital device which includes a tubular body having a tongue at one end for surrounding and supporting a penis. U.S. Pat. No. 3,982,530 (Storch) discloses a penial appliance which includes a base and four elongated support members extending from the base which cover the tip of a penis and extend along a substantial length of the sides of the penis.

U.S. Pat. No. 1,133,958 (Henderson) discloses a therapeutic truss which is transversely passed over a penis to entrap blood in the penis to thereby enlarge its size.

U.S. Pat. No. 1,462,000 (Bennett) discloses a splint which is positioned adjacent to the ventral side of a penis and which is secured to the penis by strings positioned at both ends of the device.

U.S. Pat. No. 837,993 (Williams) discloses a tubular brace for a penis. U.S. Pat. No. 1,511,572 (Marshall) and U.S. Pat. No. 4,022,196 (Clinton) disclose penial prosthetic devices which are secured to the wearer's body by a belt and include a base having a circular aperture and support structure coupled to the base for supporting the outer end of a penis.

U.S. Pat. No. 3,832,966 (Kalnberz) discloses an endoprosthesis for a penis which is surgically implanted within a penis to substantially increase the rigidity of a penis.

SUMMARY OF THE INVENTION

The present invention contemplates an externally applied support for a penis comprising a curved base formed from or configured as a section of a resilient tubular member having a first radius equal to the radius of the penis. The base includes first and second sides. A resilient first side member is coupled to the first side of the base. The first side member is formed from or configured as a second section of the tubular member and includes first and second laterally symmetrical brace elements which helically sweep above and away from the base and are adapted to partially support and encircle a first side of the penis. A resilient second side member is coupled to the second side of the base. The second side member is formed from or configured as a third section of the tubular member and includes first and second laterally symmetrical brace elements which helically sweep above and away from the base and are adapted to partially encircle and support a second side of the penis. The second side of the penis is diametrically opposed to the first side of the penis.

DESCRIPTION OF THE DRAWING

The invention is pointed out with particularity in the appened claims. However, other objects and advantages, together with the operation of the invention, may be better understood by reference to the following detailed description taken in connection with the following illustrations wherein:

DESCRIPTION OF THE PREFERRED EMBODIMENT

In order to better illustrate the advantages of the present invention and its contributions to the art, a preferred hardware embodiment of the invention will now be described in some detail.

Figure 1:
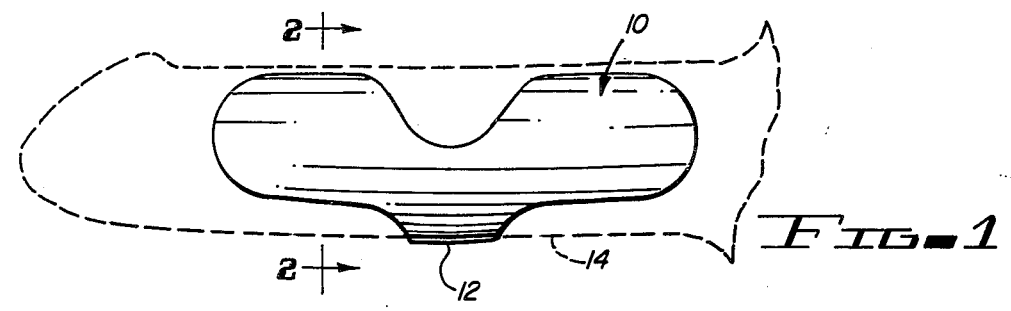
FIG. 1 is a side view of the present invention, particularly illustrating the manner in which the device is coupled to a penis.
Figure 2:
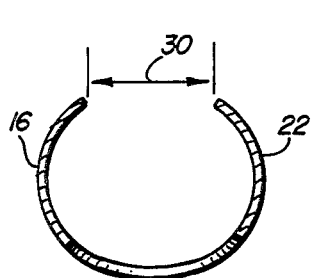
FIG. 2 is a sectional view of the support shown in FIG. 1, taken along Section line 2—2.
Figure 3:
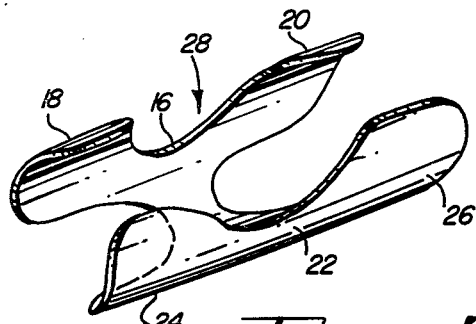
FIG. 3 is a perspective view from above of the present invention.

Referring now to FIG. 1, support 10 of the present invention includes a curved base 12 which is positioned adjacent to the ventral side 14 of a penis as shown.

The support of the present invention can be fabricated in many different diameters and lengths, but in the preferred embodiment is fabricated from a 2¾ inch section of ABS or PVC pipe having a 15/16 inch inner diameter. The support may also be formed from a plastic material which has been molded into the desired substantially tubular geometric configuration. Referring now to the figures generally, a resilient first side member 16 joins one side of base 12 and includes first and second laterally symmetrical brace elements 18 and 20. Brace elements 18 and 20 helically sweep above and away from base 12 and are adapted to partially support and encircle one side of the penis.

A second side member 22 joins the second side of base 12 and includes first and second laterally symmetrical brace elements 24 and 26. Brace elements 24 and 26 helically sweep above and away from base 12 and are adapted to partially encircle and support the second side of the penis at a point which is diametrically opposite to the portion of the penis supported by first side members 16.

If the present invention is fabricated from tubular PVC pipe, the wall thickness must be reduced by sanding or an equivalent procedure to approximately 0.040 to 0.045 inches. It has been found that this particular range of wall thickness provides the maximum trade off between mechanical strength and resiliency. As a result of this comparatively small wall thickness dimension, the support of the present invention readily flexes radially inwardly and radially outwardly to permit the device to expand to facilitate initial fitting to a penis.

First side member 16 and second side member 22 are typically mirror images of one another. Each side member is generally vertically disposed and includes a downwardly extending notch indicated by arrow 28. The notches in the first and second side members are generally U-shaped in configuration and are approximately equivalent to an arc of a ⅜ inch radius. circle.

Figure 5:
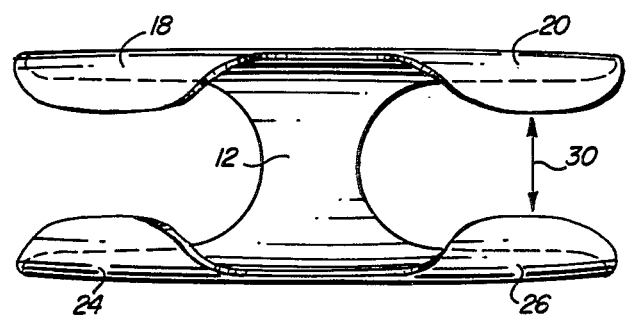
FIG. 5 is a view of the present invention from above.
Figure 4:
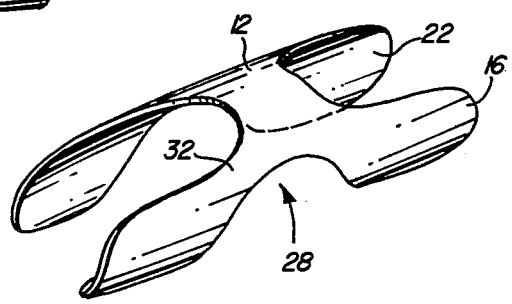
FIG. 4 is a perspective view of the bottom side of the present invention.
Figure 6:
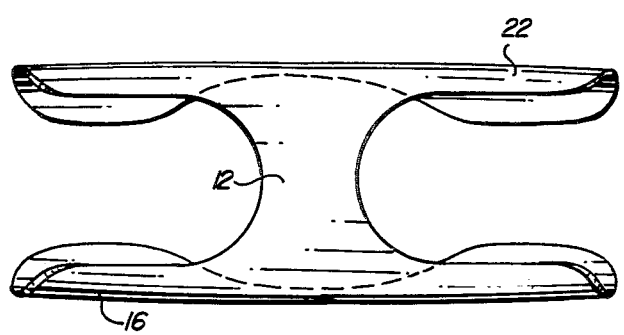
FIG. 6 is a view of the present invention from below.

As can be seen most clearly from FIG. 5, a substantial gap indicated by the line designated by reference number 30 is maintained below the upper sections of first side member 16 and second side member 22. This gap is provided to maximize the exposure of the dorsal side of the penis. The notches designated by arrow 28 are provided to serve a similar function.

In the preferred embodiment having a 15/16 inch inner diameter, gap 30 has a dimension of approximately ⅝ inch. If properly manufactured, when the dimension of gap 30 is increased to ¾ inches, an inward spring tension of approximately four ounces will be produced. When the dimension of gap 30 is increased to one inch, a spring tension of approximately six ounces will be produced. For the particular size support described above, inward tensions less than those described above may permit the support to be displaced from the penis during sexual intercourse. Substantially greater return forces may cause wearer discomfort.

During the manufacturing process, all edges and corners of the support are smoothly rounded and the outer walls of the device are polished. All interior surfaces of the support are provided with a dull surface to maximize frictional contact between the interior surface of the support and the exterior surface of the penis.

The support of the present invention should be washed in soap and water and dryed prior to initial use. The interior surfaces of the support should be maintained clean and dry and should not be lubricated. The support is fitted about the penis as illustrated in FIG. 1 prior to engaging in sexual intercourse. An ample supply of lubricating fluid is applied around and within the female gential areas, but should not be applied to any portion of the penis or support. To initiate sexual intercourse, the female partner should carefully insert the penis and support assembly within her vagina in a manner which permits both the male and female to be as comfortable as possible. Following completion of intercourse, the support should be removed and washed with soap and water.

The unique structure of the present invention permits not only flexibility in the radial direction, but also allows torsional flexion of the first side member 16 with respect to second side member 22 as a result of the ability of base 12 to permit and withstand twisting. Similarly, the thin support section, such as support section 32, assist in permitting radial expansion and contraction of brace elements 20 and 26 independently of radial expansion and contraction of brace elements 18 and 24. The unique structure of the present invention permits an unexpected degree of flexibility and freedom for the wearer while continuously maintaining firm longitudinally directed support forces which maintain a penis in a generally erect configuration.

It will be apparent to those skilled in the art that the disclosed support may be modified in numerous ways and may assume many embodiments other than the preferred form specifically set out and described above. For example, numerous different materials such as ABS plastic may be used instead of the PVC previously disclosed. The general shape and configuration of the device has been configured to maximize the structural support while minimizing the external area of the penis which is covered by the device. It will be readily apparent that the external configuration of the support may be modified in numerous ways while still falling within the general scope and intent of the teachings of the present invention. Accordingly, it is intended by the appended claims to cover all such modifications of the invention which fall within the true spirit and scope of the invention.

I claim:

1. An externally applied support for a penis comprising:
    a. a curved base formed as a section of a resilient tubular member having a first radius equal to the radius of said penis, said base having first and second sides;
    b. a resilient first side member coupled to the first side of said base, formed as a second section of said tubular member and having first and second laterally symmetrical brace elements helically sweeping above and away from said base and adapted to partially support and encircle a first side of said penis; and
    c. a resilient second side member coupled to the second side of said base, formed as a third section of said tubular member and having first and second laterally symmetrical brace elements helically sweeping above and away from said base and adapted to partially encircle and support a second side of said penis, the second side of said penis being diammetrically opposed to the first side.

2. The support of claim 1 wherein said first side member is a mirror image of said second side member.

3. The support of claim 2 wherein said base is placed adjacent to the ventral side of said penis.

4. The support of claim 3 wherein said first side member is generally vertically disposed and includes upper and lower sections and wherein said second side member is generally vertically disposed and includes upper and lower sections.

5. The support of claim 4 wherein the midportion of the upper sections of said first and second side members includes a downwardly extending notch.

6. The support of claim 5 wherein said notches are generally U-shaped in configuration, said U-shaped notches being laterally symmetrical with respect to said first and second brace elements.

7. The support of claim 1 wherein said support is formed from plastic.

8. The support of claim 7 wherein said plastic support is formed from a section of tubular PVC pipe.

9. The support of claim 7 wherein said plastic support is formed from a section of tubular ABS pipe.

10. The support of claim 1 wherein a substantial gap is maintained between the upper sections of said first and second side members to expose a substantial portion of the dorsal side of said penis.

11. The support of claim 10 wherein the length of said base is substantially less than the length of said first and second side members.

12. The support of claim 11 wherein the length of said base is less than one third of the length of said side members.

13. An externally applied support for a penis comprising:

a. a curved base formed as a section of a resilient tubular member having a first radius equal to the radius of said penis, said base having first and second sides and positioned adjacent to the ventral side of said penis;

b. a resilient first side member coupled to the first side of said base, formed as a second section of said tubular member and having first and second laterally symmetrical brace elements helically sweeping above and away from said base and adapted to partially support and encircle a first side of said penis, said first side member being generally vertically disposed and including upper and lower sections, the midportion of the upper section including a downwardly extending notch; and c. a resilient second side member coupled to the second side of said base, formed as a third section of said tubular member and having first and second laterally symmetrical brace elements helically sweeping above and away from said base and adapted to partially encircle and support a second side of said penis, the second side of said penis being diametrically opposed to the first side, said second side member being generally vertically disposed and including upper and lower sections, the midportion of the upper section including a downwardly extending notch.

14. The support of claim 13 wherein the notches in said first and second side members are generally U-shaped in configuration and are laterally symmetrical with respect to the first and second brace elements of said first and second side members.

15. The support of claim 14 wherein said support is formed from plastic.

* * * * *